(12) United States Patent
Thompson et al.

(10) Patent No.: US 10,383,819 B1
(45) Date of Patent: Aug. 20, 2019

(54) METHOD TO EFFECT BIPHASIC BIOAVAILABILITY OF ORAL EUPHORIC PSYCHOGENIC CANNABINOIDS

(71) Applicants: Ronald J. Thompson, Cincinnati, OH (US); James M. Thompson, Cincinnati, OH (US)

(72) Inventors: Ronald J. Thompson, Cincinnati, OH (US); James M. Thompson, Cincinnati, OH (US)

(73) Assignee: Callitas Therapeutics, Inc., Newport, KY (US)

( * ) Notice: Subject to any disclaimer, the term of this patent is extended or adjusted under 35 U.S.C. 154(b) by 0 days.

(21) Appl. No.: 16/350,351

(22) Filed: Nov. 5, 2018

Related U.S. Application Data

(60) Provisional application No. 62/764,244, filed on Jul. 23, 2018.

(51) Int. Cl.
| | |
|---|---|
| *A61K 9/00* | (2006.01) |
| *A61K 47/18* | (2017.01) |
| *A61K 47/10* | (2017.01) |
| *A61K 31/352* | (2006.01) |

(52) U.S. Cl.
CPC .......... *A61K 9/0056* (2013.01); *A61K 31/352* (2013.01); *A61K 47/10* (2013.01); *A61K 47/183* (2013.01)

(58) Field of Classification Search
CPC .... A61K 9/0056; A61K 47/183; A61K 47/10; A61K 31/352
See application file for complete search history.

(56) References Cited

U.S. PATENT DOCUMENTS

| | | | |
|---|---|---|---|
| 5,989,535 A | 11/1999 | Smith | |
| 6,383,513 B1 | 5/2002 | Watts et al. | |
| 7,025,992 B2 | 4/2006 | Whittle | |
| 7,906,140 B2 | 3/2011 | Bromley et al. | |
| 7,968,594 B2 | 6/2011 | Guy et al. | |
| 10,004,684 B2 | 6/2018 | Whittle et al. | |
| 2011/0136815 A1* | 6/2011 | Zerbe | A61K 9/006 |
| | | | 514/249 |
| 2017/0333505 A1 | 11/2017 | Gharib et al. | |
| 2018/0193392 A1 | 7/2018 | Silver | |

OTHER PUBLICATIONS

Huestis, Human Cannabinoid Pharmacokinetics, 2007, Chem Biodivers., 4(8), 1770-1804, 35 pages. (Year: 2007).*
Bachhuber et al, Medical Cannabis Laws and Opioid Analgesic Overdose Mortality in the United States, 1999-2010, 2014, JAMA Internal Med., 174(10), 1668-1673. (Year: 2014).*
McHugh et al, Assessing craving and its relationship to subsequent prescription opioid use among treatment-seeking prescription opioid dependent patients, 2014, Drug and Alcohol Dependence, 145, pp. 121-126. (Year: 2014).*

* cited by examiner

*Primary Examiner* — Trevor Love
(74) *Attorney, Agent, or Firm* — Don Halgren

(57) ABSTRACT

A method to effect biphasic bioavailability of oral euphoric psychogenic cannabis. The method comprises the step of providing and ingesting a chambered, layered oral drug delivery arrangement, to achieve both a rapid systemic euphoric cannabis effect, and a delayed, but sustained, systemic cannabis euphoric effect.

15 Claims, No Drawings

METHOD TO EFFECT BIPHASIC BIOAVAILABILITY OF ORAL EUPHORIC PSYCHOGENIC CANNABINOIDS

FIELD OF THE INVENTION

The field of the present invention is generally human drug delivery and systemic drug bioavailability, and specifically, biphasic oral drug delivery of euphoric psychogenic cannabinoids, for both immediate, and delayed and extended psychogenic cannabinoid actions, and is based upon Provisional Application No. 62/764,244 filed Jul. 23, 2018, and is incorporated herein by reference in its entirety.

ABSTRACT

The present invention is a method to utilize a combination of a rapidly dissolving formulation, and an edible non-dissolving chocolate, or gummy matrix, for an individual to self-administer psychogenic cannabinoids, delta-9 tetrahydrocanabinol, THC, and 11-hydroxy tetrahydrocannabinol, 11-OH THC. The orally dissolving formulation containing menthol, 1-arginine, and THC is for enhanced THC bioavailability, and for an immediate THC psychogenic effect like inhaling cannabis. The edible chocolate or gummy matrix containing THC as a prodrug is chewed, ingested, and enterically digested and absorbed. The absorbed THC as a prodrug is liver-converted into an active metabolite of THC, 11-OH THC, a long lasting, potent metabolite of THC that provides psychogenic actions from 2 hours after ingestion, for about 10-15 hours. The present invention, with both immediate and prolonged THC psychogenic euphoric actions, could serve as a safe opioid alternative, and impact the current opioid overdose epidemic. THC does not cause respiratory depression and overdose deaths, as do the opioids.

APPLICATION BASED UPON

Provisional U.S. Patent Application No. 62/579,212, filed 31 Oct. 2017, "Orally dissolving mucoadhesive films utilizing menthol and 1-arginine to enhance the bioavailability of cannabinoids" and its non-provisional application, Ser. No. 16/350,001, filed 12 Sep. 2018, and all resultant art, are incorporated herein by reference in their entirety.

Background Cannabinoids

There are three major cannabinoids: cannabidiol (CBD), delta-9 tetrahydrocannabinol (THC), and 11-hydroxy tetrahydrocannabinol (11-OH THC). All three cannabinoids are anti-inflammatory agents, but only THC and 11-OH THC are euphoric psychogenic agents, as well as anti-inflammatory agents. CBD can generally be ingested as a pill, oil, tincture, or as a candy or in an edible such as a chocolate or gummy candy, or a cookie or brownie. CBD is Medical Marijuana because of it's anti-inflammatory actions.

THC can be inhaled, by smoking or vaporizing, and ingested as a pill, oil, tincture, or as an edible. 11-OH THC is not commercially available. 11-OH THC is the liver converted active metabolite of ingested THC. THC must be ingested, digested, and absorbed by the small intestines, before being presented to the liver for enzymatic conversion into 11-OH THC. Ingested THC is the prodrug of 11-OH THC.

| US States/Date Allowing Legal Marketing of Recreational/Adult Use Cannabis (Products containing THC) | | |
|---|---|---|
| State | Population | Allow Public Smoking of Cannabis |
| CA 2018 | 37M | NO |
| CO 2012 | 5M | NO |
| AZ 2018 | 6.4M | NO |
| OR 2015 | 3.8M | NO |
| WA 2014 | 6.7M | NO |
| MA 2018 | 6.5M | NO |
| AK 2017 | 0.7M | NO |

Psychogenic and non-psychogenic cannabis are currently federally illegal. The above states have legalized recreational use, or adult use, cannabis, by popular majority vote. The US FDA is granted the authority of controlling the inter-state transportation and marketing of cannabis, but not the intra-state marketing and production of cannabis.

No State currently allows the public smoking of cannabis.

BRIEF SUMMARY OF THE PRESENT INVENTION

The present invention is a method for manifesting biphasic bioavailability of THC, by inducing both an immediate euphoric psychogenic effect from orally administered THC, like inhaling or smoking cannabis, and a delayed, prolonged THC euphoric effect like a cannabis edible, where the THC is a prodrug for 11-OH THC. This method is biphasic, and utilizes a two stage drug delivery technology, the first stage with enhanced oral THC absorption.

The invention thus comprises a method to effect biphasic bioavailability of oral euphoric psychogenic cannabis comprising: ingesting a chambered, layered oral drug delivery arrangement, to achieve both a rapid systemic euphoric cannabis component effect, and a delayed, but sustained, systemic cannabis component euphoric effect. The euphoric cannabis component is an effective amount of delta-9 tetrahydrocannabinol (THC) of between 5 mg and 20 mg and are both contained within the chamber, and is a component of the chamber defining edible matrix. The chamber, is created and defined by an outer edible arrangement of gummy candy, hard candy, or chocolate candy, containing an effective amount of THC. The chamber houses a liquid formulation of an effective amount of water soluble THC (between 5 mg and 20 mg), menthol (between 0.1 mg and 1.0 mg), and 1-arginine (between 1 mg and 5 mg). The outer edible gummy candy, hard candy, or chocolate candy, is crushed in the oral cavity, and the chamber orally liberates and releases an effective amount of water soluble THC, menthol and 1-arginine into the buccal cavity. The orally released water soluble THC, menthol and 1-arginine are rapidly absorbed from the buccal mucous membrane, into the systemic circulation, to achieve a rapid euphoric cannabis effect. The chamber defining material is an edible like gummy candy, hard candy, or hard chocolate containing within the matrix an effective amount of THC, a prodrug for the liver conversion into 11-Hydroxytetrahydrocannabinol (11-OH-THC), the active metabolite of THC, for systemic sustained cannabis component euphoric effects.

The invention also includes a method to effect biphasic bioavailability of oral euphoric psychogenic cannabis comprises: ingesting a bi-layered oral drug delivery arrangement comprising an outer rapid drug delivery layer, to achieve both a rapid euphoric cannabis effect, and an inner delayed, sustained drug delivery layer, creating a systemic cannabis euphoric effect. The psychogenic euphoric cannabis contained within both the outer drug delivery layer and the inner delayed sustained drug delivery layer, is an effective amount of delta-9-tetrahydrocannabinol (THC). The dissolvable outer layer contains an effective amount of THC, menthol and 1-arginine. The outer layer dissolves in the oral cavity, and releases the THC, menthol and 1-arginine, for mucous membrane absorption of THC, menthol, and 1-arginine into the systemic circulation for a rapid cannabis euphoric effect. The inner layer is selected from the group comprising: an edible-like gummy candy, hard candy, or hard chocolate containing an effective amount of THC. The edible containing an effective amount of THC is normally digested and absorbed by the small intestines into the portal (liver) circulation. The effective amount of THC is a prodrug and is liver converted into 11-Hydroxytetrahydrocannabinol (11-OH-THC) the active metabolite of THC, and systemically circulated for a sustained cannabis euphoric effect. The method includes effecting biphasic bioavailability of oral psychogenic euphoric cannabis with both a rapid cannabis effect, and a delayed, yet sustained cannabis effect, as a safe alternative to opioid use.

DESCRIPTION OF THE PRESENT INVENTION: ARRANGEMENTS

There are at least TWO different arrangements to effect biphasic bioavailability of oral THC. With the first arrangement, positioning the rapidly dissolving/enhanced THC absorption/bioavailability first stage as the outer layer, much like the hard outer covering of a "tootsie roll pop". The second arrangement would contain the rapidly dissolving/enhanced THC absorption/bioavailability first stage within a chamber like a "chocolate cherry cordial". In both arrangements, the first stage would also contain menthol for mucous membrane enhanced THC permeation/THC absorption and bioavailability. The first stage of both arrangements would also contain 1-arginine to effect submucosal vasodilitation and enhanced THC absorption and bioavailability.

The second stage of a chewable, digestable THC containing chocolate, would not contain menthol or 1-arginine. The second stage of the "tootsie roll pop" would be the chewable chocolate center. The second stage of the "chocolate cherry cordial" would be the chewable hard outer chocolate shell. Both arrangements of the second stage would only contain an effective dosage of THC, for digestion, absorption into the portal vein, and liver conversion into 11-OH-THC.

The First Stage of the THC Absorption—Oral Cavity

The enhanced oral THC absorption is accomplished by utilizing menthol and 1-arginine as permeation enhancement, and vasodilation agents with the THC. This enhanced drug delivery, and oral THC absorption, occurs within the entire oral cavity, and interfaces with all mucous membrane surfaces of the buccal cavity. The orally administered menthol, 1-arginine, and THC rapidly dissolves in the oral saliva, and coats the entire buccal cavity. The almost immediate absorption of THC, and systemic bioavailability of THC mirrors inhaling or smoking cannabis. FIG. 1 of Human Cannabinoid Pharmacokinetics, by Marilyn A. Huestis, (www.pubmed.gov/17712819) published as *Chem Biodivers.* 2007 August: 4(8): 1770-1804. Doi:[10.1002/cbdv.200790152], incorporated herein by reference in its entirety, shows that smoking 3.55% THC cannabis produces a rapid rise of plasma THC, from 0 to 150 micrograms/ml in 10 minutes. This is with 8 inhalations over 10 minutes, in 6 patients. The menthol/1-arginine enhanced oral mucous membrane absorption of THC is about 70% of the efficacy of smoked/inhaled THC, and also occurs in a 10-15 minute window. The method entails maintaining the menthol/1-arginine/THC coated edible THC in the oral cavity for about 10 minutes before chewing the edible.

FIG. 1 of *Chem Biodiverse*, cited and referenced hereinabove, also defines that inhaled or smoked THC is not metabolized into 11-OH THC, only ingested/digested THC can be converted into 11-OH THC.

The orally absorbed THC impacts the Endocannabinoid System as a retrograde neurotransmitter, and produces a euphoric effect for multiple hours, 4-8, depending upon THC dosage.

The Second Stage: THC Conversion into 11-OH THC

After the first stage has dissolved, and the oral THC absorbed systemically, the edible component is chewed, ingested, and then digested in the duodenum and small intestines. This requires several hours, and is influenced by stomach contents. The THC containing digested edible is absorbed, and transported to the liver where the THC is converted into 11-OH THC. THC is a prodrug for 11-OH THC. 11-OH THC is the active metabolite of THC, and has a pronounced and prolonged euphoric effect.

FIG. 3 of Human Cannabinoid Pharmakinetics from *Chem Biodiverse* cited hereinabove and again incorporated herein by reference in its entirety, shows that the 11-OH THC can produce an effect up to 15 hours after ingestion, with a maximum effect of 110 micrograms/ml 6 hours after ingestion. The 11-OH THC continuously impacts the Endocannabinoid System while the plasma THC concentrations are elevated. This produces a prolonged euphoric effect.

The biphasic THC bioavailability, rapid oral absorption of THC, and the delayed, subsequent conversion of THC into 11-OH THC, provide both an immediate euphoric state and an extended euphoric state, 12-18 hours, that could provide a safe drug alternative to opioids. Opioids cause respiratory depression and overdose deaths from respiratory depression relative to opioid dose. This is the rationale of the second reference, and the reason that Massachusetts prioritized recreational cannabis dispensary licenses to areas of high opioid overdose deaths. Cannabis, THC, or 11-OH THC do not cause respiratory depression.

Again from FIG. 3, "Human Cannabinoid Pharmacokinetics", found in *Chem Biodiverse* cited hereinabove and again incorporated herein by reference in its entirety, shows the 11-OH-THC has a prolonged plasma concentration peak effect from 5 hours after ingestion of the THC, to 10 hours after ingestion of THC. The 11-OH-THC plasma concentration at this peak effect is double the peak effect of THC plasma concentration. The area under the curve (AUC) comparison of plasma concentrations of THC and 11-OH-THC shows that the 11-OH-THC is triple the plasma concentration of THC. In addition, the plasma concentration of 11-OH-THC is prolonged for over 24 hours, as compared to only 12 hours for the THC. The plasma concentration of the THC is responsible for the systemic cannabinoid effects, including euphoria.

The invention claimed is:

1. A method to effect biphasic bioavailability of oral euphoric psychogenic cannabis comprising: ingesting a chambered, layered oral drug delivery arrangement, to achieve both a rapid systemic euphoric cannabis effect, and a delayed, but sustained, systemic cannabis euphoric effect,
    wherein the chamber is created and defined by an outer edible arrangement of gummy candy, hard candy, or chocolate candy containing an effective amount of THC between 5 mg and 20 mg, and
    wherein the chamber houses a liquid formulation of an effective amount of water soluble THC between 5 mg and 20 mg, menthol between 0.1 mg and 1.0 mg, and 1-arginine between 1 mg and 5 mg.

2. The method of claim 1, where the euphoric cannabis is an effective amount of delta-9 tetrahydrocannabinol (THC) and is both contained within the chamber, and is a component of the chamber defining edible matrix.

3. The method of claim 1, where the outer edible gummy candy, hard candy, or chocolate candy, is crushed in the oral cavity, and the chamber orally liberates and releases an effective amount of water soluble THC, menthol and 1-arginine into the buccal cavity.

4. The method of claim 1, where the orally released water soluble THC, menthol and 1-arginine are rapidly absorbed from the buccal mucous membrane, into the systemic circulation, to achieve a rapid euphoric cannabis effect.

5. The method of claim 1, where the chamber defining material is an edible like gummy candy, hard candy, or hard chocolate containing within the matrix an effective amount of THC, a prodrug for the liver conversion into 11-Hydroxytetrahydrocannabinol (11-OH-THC), the active metabolite of THC, for systemic sustained cannabis euphoric effects.

6. A method to effect biphasic bioavailability of oral euphoric psychogenic cannabis comprises: ingesting a bi-layered oral drug delivery arrangement comprising an outer rapid drug delivery layer, to achieve both a rapid euphoric cannabis effect, and an inner delayed, sustained drug delivery layer, creating a systemic cannabis euphoric effect,
wherein the oral drug delivery arrangement is in the form of a gummy candy, hard candy, or chocolate candy containing an effective amount of THC between 5 mg and 20 mg, and
wherein the gummy candy, hard candy, or chocolate candy houses a liquid formulation of an effective amount of water soluble THC between 5 mg and 20 mg menthol between 0.1 mg and 1.0 mg, and 1-arginine between 1 mq and 5 mg.

7. The method of claim 6, where the psychogenic euphoric cannabis contained within both the outer drug delivery layer and the inner delayed sustained drug delivery layer, is an effective amount of delta-9-tetrahydrocannabinol (THC).

8. The method of claim 6, where the dissolvable outer layer contains an effective amount of THC, menthol and 1-arginine.

9. The method of claim 6, where the outer layer dissolves in the oral cavity, and releases the THC, menthol and 1-arginine, for mucous membrane absorption of THC, menthol, and 1-arginine into the systemic circulation for a rapid cannabis euphoric effect.

10. The method of claim 6, where the inner layer is selected from the group comprising: an edible-like gummy candy, hard candy, or hard chocolate containing an effective amount of THC.

11. The method claim 10, where the edible containing an effective amount of THC is normally digested and absorbed by the small intestines into the portal (liver) circulation.

12. The method of claim 11, where the effective amount of THC is a prodrug and is liver converted into 11-Hydroxytetrahydrocannabinol (11-OH-THC) the active metabolite of THC, and systemically circulated for a sustained cannabis euphoric effect.

13. The method of claim 7, wherein the effective amount of THC is between 5 mg and 20 mg.

14. The method of claim 8, wherein the effective amount of THC is between 5 mg and 20 mg, and wherein the effective amount of menthol is between 0.1 mg and 1.0 mg, and wherein the effective amount of 1-arginine is between lmg and 5 mg.

15. A method to effect a safe alternative to opioid use; the method comprising: ingesting a biphasic bioavailable oral psychogenic euphoric cannabis, the cannabis having both a rapid cannabis component effect and a delayed, yet sustained cannabis component effect as the alternative to opioid use,
wherein the oral psychogenic euphoric cannabis being in the form of a gummy candy, hard candy, or chocolate candy containing an effective amount of THC between 5 mg and 20 mg, and
wherein the gummy candy, hard candy, or chocolate candy houses a liquid formulation of an effective amount of water soluble THC between 5 mg and 20 mg, menthol between 0.1 mg and 1.0 mg, and 1-arginine between 1 mg and 5 mg.

* * * * *